United States Patent [19]

Fenne et al.

[11] 4,387,468
[45] Jun. 7, 1983

[54] MOBILE X-RAY APPARATUS

[75] Inventors: Kenneth R. Fenne, Glen Ellyn; Carl A. Wassell, Streamwood, both of Ill.

[73] Assignee: Techny Industries, Inc., Glenview, Ill.

[21] Appl. No.: 310,077

[22] Filed: Oct. 9, 1981

[51] Int. Cl.³ .............................................. A61B 6/00
[52] U.S. Cl. .................................................. 378/198
[58] Field of Search ....................................... 378/198

[56] References Cited

U.S. PATENT DOCUMENTS 2,041,242 5/1936 Goldfield ............................ 378/198
3,790,005 2/1974 Foderaro ............................ 378/198

OTHER PUBLICATIONS

Mobile Masters 30 brochure of Universal X-Ray, publication date unknown.
"pixie" Mobile X-Ray unit brochure of Porta Ray Inc., publication date unknown.

Primary Examiner—A. E. Smith
Assistant Examiner—T. N. Grigsby
Attorney, Agent, or Firm—Trexler, Bushnell & Wolters, Ltd.

[57] ABSTRACT

A mobile X-ray apparatus comprises a base and a column on the base and rotatable about a vertical axis. A carriage is mounted for upward and downward movement on the column and an arm is mounted on the carriage for movement therewith. On one end of the arm is an X-ray tube head assembly which is rotatable with the column about its vertical axis throughout a 180°. The tube head assembly is counterweighted by an X-ray film cassette bin plus control circuitry for operating the X-ray tube, together with the housing for the control circuitry. The tube head assembly may be placed in a storage and transport position in which the tube head is well within the confines of the base of the unit, thereby contributing to the stability of the unit.

4 Claims, 16 Drawing Figures

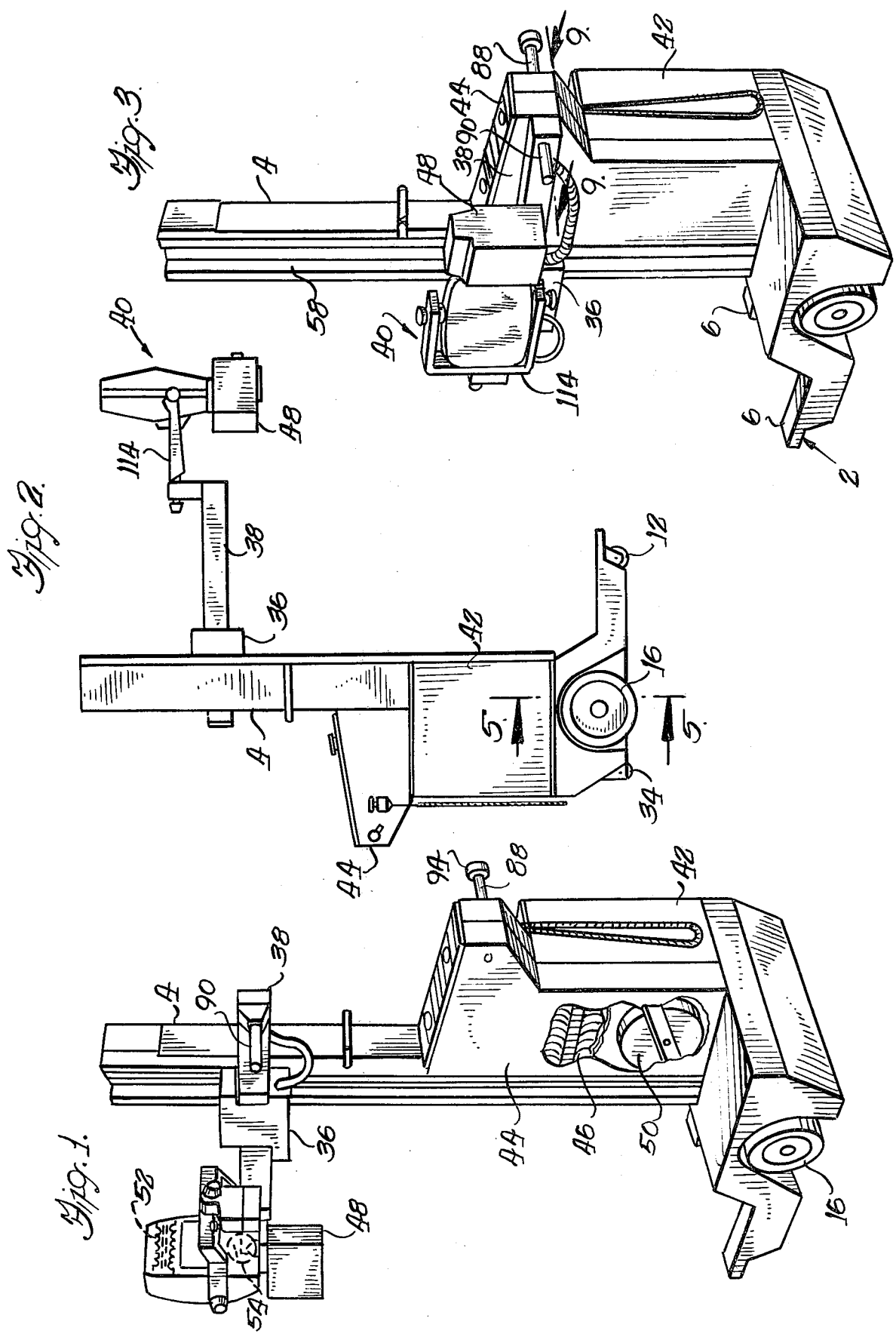

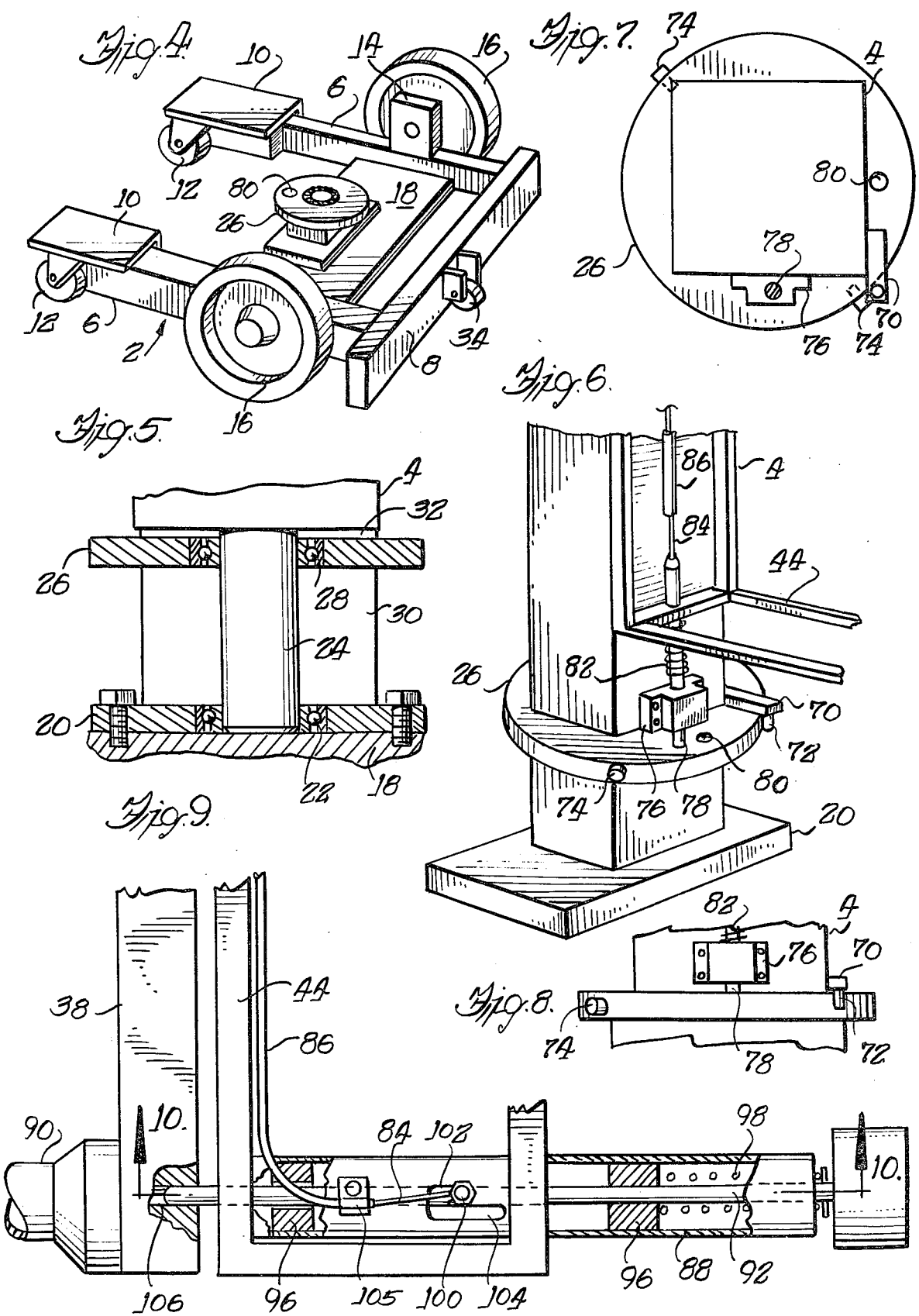

MOBILE X-RAY APPARATUS

BACKGROUND OF THE INVENTION

This invention relates to a mobile X-ray apparatus for the type used in hospitals, skilled-care nursing homes, and like institutions, and which is utilized to obtain radiographs of bed-ridden patients.

In hospitals and like institutions it is a common practice to provide mobile X-ray systems of the type that can be transported and readily positioned at bedside in order to obtain radiographs. Prior art commercially available units of this type frequently have limitations as to maneuverability and flexibility of operation. Such units tend to be clumsy and are often excessively heavy, requiring a power drive in order to move the unit from place-to-place. Furthermore, the design of the unit is such that there are limitations as to movement of the X-ray tube head. Such limitations frequently preclude moving the tube head too far to either side of the supporting base because if moved too far the weight of the tube head may render the unit unstable, causing it to tip over. Also, restrictions on rotation or swinging of the tube head limits the range of positioning of the tube head relative to a bed-ridden patient, thereby creating difficulties for the X-ray technician who is attempting to position the tube head at a precise location. Furthermore, the design of many commercially available mobile X-ray units is such that the units occupy an excessively large amount of floor area making it difficult to position the unit properly where there are narrow spacings between hospital beds.

OBJECTS AND SUMMARY OF THE INVENTION

An object of the present invention is to provide a mobile X-ray unit of the type in which the tube head includes the X-ray tube and the X-ray transformer and wherein the unit is light weight and highly maneuverable, requiring no power drive. On the contrary, the unit may be transported and positioned at bedside by a single person with a minimum of time, motion, and effort.

It is a further and more specific object of this invention to provide a mobile X-ray apparatus of the type stated that occupies only a relatively small amount of floor area, which allows working over the bed from virtually any approach or angle including narrow spacings between beds. This feature of the invention is aided by the fact that the X-ray tube head can be shifted through a wide range of positions while at the same time the unit remains in a condition of stable support on the floor.

More particularly, the invention provides for maintaining even weight distribution to offset or counterbalance the tube head at its extreme positions of transverse and vertical movement. This counterbalancing weight is uniquely provided by a cassette bin and control cabinet assembly which are mounted on the rear of the tube column opposite to the tube head and which rotates with the tube column about its vertical axis.

Still another object of this invention is to provide an apparatus of the type stated in which the tube head may be positioned in a storage and transport position such that the tube head is primarily within the confines of the floor space occupied by the transport base. This arrangement provides stability and ease of movement of the unit. In accordance with the foregoing objects the invention comprises a mobile X-ray apparatus having a base with a front and opposed sides, floor-engaging wheels on the base adjacent to the front and sides, a column on said base and being rotatable about a vertical axis, a carriage mounted for upward and downward movement on the column, an X-ray tube arm mounted on said carriage for movement therewith, said arm also being movable on said carriage generally horizontally relative to said base, the extent of horizontal movement of said arm and the extent of rotation of said column being such as to position an end of said arm in a number of extended locations outboard of said front and sides, an X-ray tube head assembly at said arm end; said assembly including an X-ray tube, and X-ray transformer, and a collimator; and counterweight means carried by said column and rotatable therewith for counterbalancing the tube arm and tube head assembly in said extended locations; said counterweight means including an X-ray film cassette bin plus control circuitry for operating said X-ray tube and a housing for said control circuitry.

BRIEF DESCRIPTION OF THE FIGURES

FIG. 1 is a perspective view of a mobile X-ray apparatus in accordance with the present invention and being shown in one of its radiographic positions;

FIG. 2 is a side elevational view of the apparatus of FIG. 1;

FIG. 3 is a perspective view similar to FIG. 1 but showing the tube head, tube arm and column in the storage and transport position;

FIG. 4 is a fragmentary perspective view of the base of the apparatus which forms part of the present invention;

FIG. 5 is a fragmentary sectional view, on an enlarged scale, taken approximately along line 5—5 of FIG. 2;

FIG. 6 is a fragmentary perspective view, on an enlarged scale, of the lower end of the tube column;

FIG. 7 is a fragmentary plan view showing a portion of the structure of FIG. 6;

FIG. 8 is a fragmentary front elevational view of the structure of FIG. 7;

FIG. 9 is a fragmentary sectional view, partially in elevation and on an enlarged scale, taken approximately along line 9—9 of FIG. 3.

DETAILED DESCRIPTION

Figure 10:
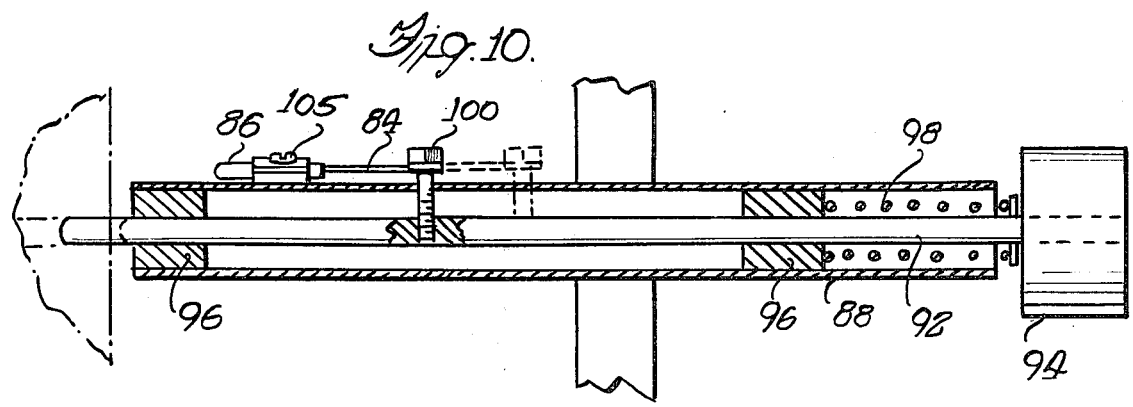
FIG. 10 is a fragmentary sectional view taken substantially along line 10—10 of FIG. 9.

Referring now in more detail to the drawing there is shown a mobile X-ray apparatus comprising a base 2 upon which is mounted, in a manner to be described, a column 4 that is rotatable about a vertical axis. The base 2 comprises a frame which includes spaced parallel legs 6, 6 and a rear or bight member 8. The forward ends of the legs 6, 6 are provided with caster plates 10, 10 to which are secured casters 12, 12. The casters 12, 12 provide a wheeled support for the front end of the frame 2, and each caster functions in a known manner. Also mounted on the legs 6, 6 forwardly of the bight 8 are bearing blocks 14, 14 (one being shown in FIG. 4) which rotatably support wheels 16, 16 outboard of the sides of the base. The wheels 16, 16 are preferably coaxial. Rigidly secured to the legs 6, 6 and extending therebetween in the region of the wheels 16, 16 is a base plate 18 for supporting a thrust bearing assembly that in turn supports the column 4.

The thurst bearing assembly includes a lower bearing retainer 20 which is bolted or otherwise rigidly secured to the plate 18. This bearing retainer 20 supports a lower bearing 22 which receives and journals the lower cylindrical end 24 of the column 4. Spaced above the retainer 20 is an upper bearing retainer 26 which houses an upper bearing 28 which is aligned with the bearing 22. The retainers 20, 26 are separated by a spacer block 30. On its upper side the bearing retainer 26 has annular thrust bearing 32 of a suitable antifriction plastic, such as a tetrafluoroethylene resin commonly sold under the tradename Teflon. The retainers 20, 26 are located such that the vertical axis of rotation of the column 8 is slightly forward of the axis of rotation of the wheels 16, 16. An auxiliary wheel 34 is journaled on the outside of the bight 8 midway between the legs 6, 6. This auxiliary wheel 34 aids in rolling the apparatus over minor floor obstructions such as thresholds, and the like.

Figure 15:
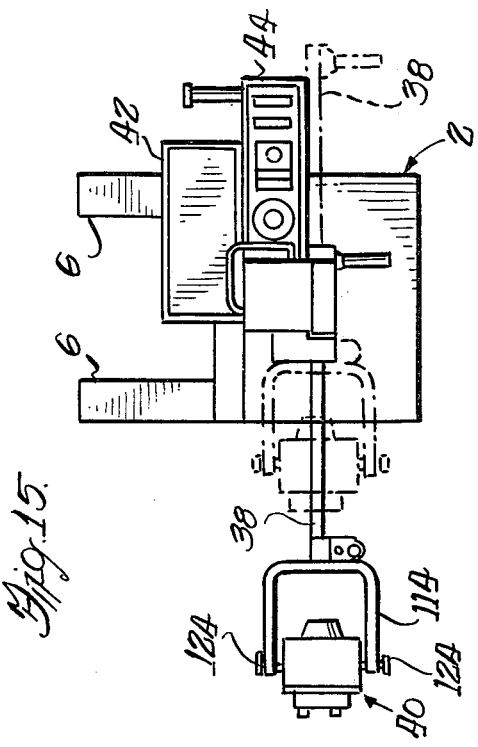
FIG. 15 is a top plan view of the apparatus and showing the tube head rotated to a position 90° counterclockwise from its normal or storage position.
Figure 16:
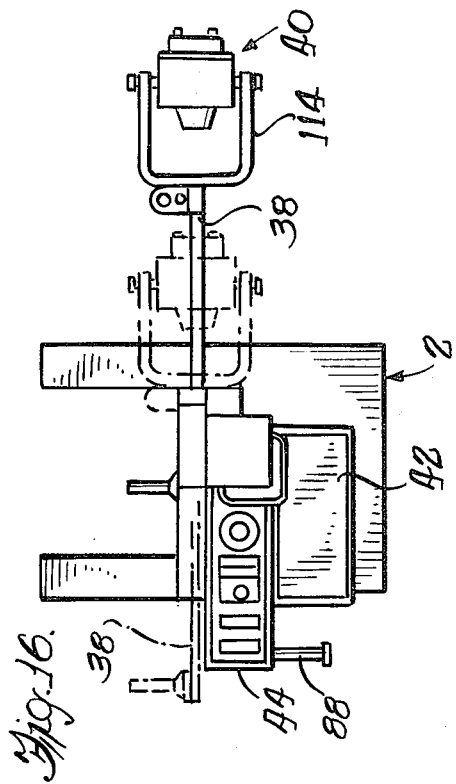
FIG. 16 is a view similar to FIG. 15 but showing the tube head rotated 90° clockwise from its storage position and which position is 180° from that shown in FIG. 15.

As the column 4 rotates it carried with it a carriage 36 which is mounted for vertical sliding movement on the column 4. The carriage 36 carries with it a tube arm 38 which slides horizontally within the carriage 36. An extended radiographic position of the apparatus is shown in FIG. 1 and extreme extended positions 180° apart are shown in full lines in FIGS. 15 and 16. An important feature of this invention lies in the fact that in the extreme extended positions shown in FIGS. 15 and 16, as well as in intermediate positions, the weight of the tube head assembly 40 and other mass outwardly of the axis of rotation of the column 4 will be counterbalanced in a unique manner.

For purposes of performing the counterweighting function, as specified above, the column 4 has secured thereto a cassette storage bin 42 which is adapted to house a number of film cassettes to be used by the technician operating the apparatus. This storage bin, whether or not filled, exerts a substantial counterweighting component force that stabilizes the apparatus in all radiographic positions. In addition to the storage bin 42 there is a housing 44 which contains control circuitry for the apparatus. This control circuitry may include the autotransformer, exposure settings circuitry, electric timer, and related circuitry. Also included is a power chassis which contains a power tansformer for the collimator 48 that is attached to and forms part of the tube head assembly 40. The power chassis may also include a power distribution panel and other circuitry. The housing 44 may also contain a line cord reel 50 with a power line cord and through which power may be supplied to the apparatus. In any case the storage bin 42 and the housing 44 are attached to and, in effect, form part of the column 4 and extend upwardly from the lower end thereof. Furthermore, the bin 42 and the housing 44 are on one side of the axis of rotation of the column 4 while the tube arm and tube head assembly 40 are on the opposite side of such axis. As a result, the housing 44 and bin 42 together with the components therein, continuously counterweight the tube arm and tube head assembly as the arm is swung between the positions shown in FIGS. 15 and 16 and even when the tube arm 38 is at its highest position of elevation on the column 4. Such an arrangement is particularly important where, as in mobile units generally, tube head assembly not only contains a collimator 56 but also an X-ray transformer 52 along with an X-ray tube 54. The tube 54 and transformer 52 are conventional, in and of themselves, and are therefore shown only schematically in FIG. 1.

In connection with this invention it should be noted that incorporating the X-ray transformer into the X-ray tube head assembly is especially desirable by reason of the development of so-called "rare earth" intensifying screens. These screens permit the use of a transformer of lower power output which can be sized for incorporation into the X-ray tube head assembly. Nevertheless, the weight of the transformer can become significant, especially when applied to a long lever arm, which would be the case where the tube arm 38 is horizontally extended the maximum permissible distance.

Figure 14:
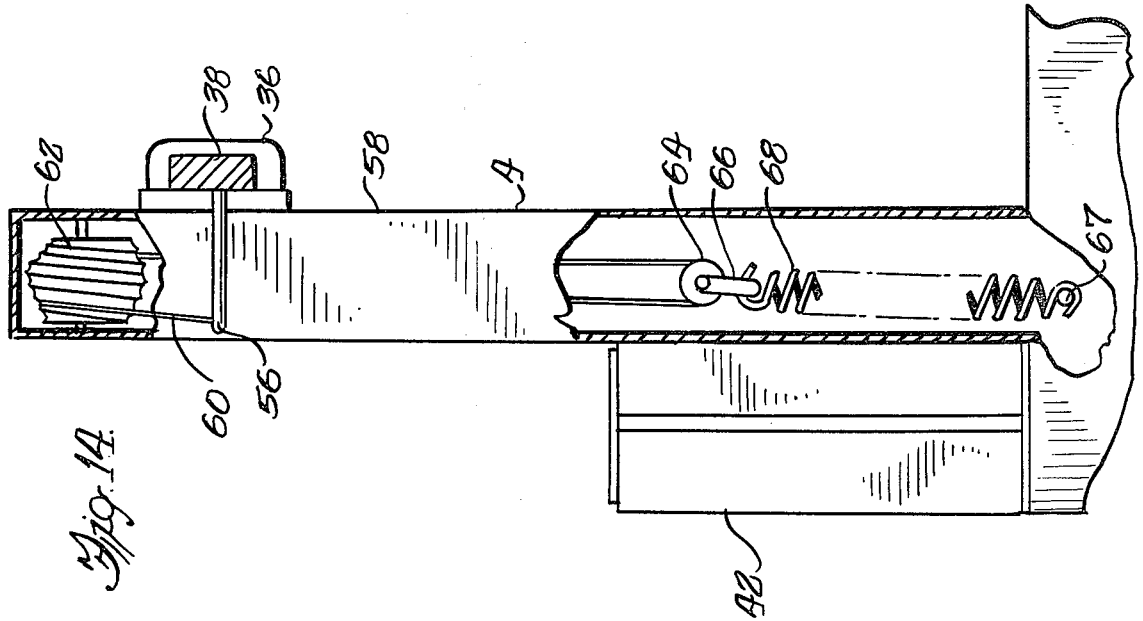
FIG. 14 is a fragmentary elevational view, partially broken away and in section, and showing the interior of the tube column to illustrate the tube arm counterbalancing means which forms part of the present invention.

The carriage 36 provides, in effect, a compound slide permitting both horizontal and vertical movement of the tube head assembly 40. Moreover, the carriage 36 includes a projection 56 (FIG. 14) which rides in a vertical slot 58 in the column 4. Projection 58 is connected to a cable 60 which forms part of a counterbalancing mechanism for the carriage 36 and the components carried thereby. The counterbalancing mechanism is known. Suffice it to say that the mechanism may consist of the cable 60 wrapped around a variable diameter compensating pulley 62, the cable also being trained around a pulley 64 and then suitably anchored to the column near the pulley 62. The pulley 64 contains a hook 66 that engages one end of a counterbalancing spring 68, the other end of which is hooked around a pin 67 at the lower end of the column 4. Thus, the spring 68 is loaded to a tension corresponding to the weight of the carriage and structure carried thereby, whereby the force exerted by the spring 68 counterbalances the weight carried by the carriage 36.

An arrangement may be provided for limiting the rotation of the column 4 to substantially 180°. As best seen in FIGS. 6–8, the lower end of the column 4 is provided with a bar 70 having a depending stop pin 72, the latter being closely adjacent to the circular outer periphery of the bearing retainer 20. At points 180° apart, the bearing retainer 20 is provided on its periphery with stop screws 74, 74 against which the stop pin 72 abuts in the extreme limits of rotation of the column 4. An arrangement may be provided for locking the column relative to the base and for locking the arm 38 in the storage and transport position, as shown in FIG. 3. At its lower end the column has suitably secured thereto a guide block 76 having a pin 78 slidable therein which is adapted to fit into an index hole 80 when the pin 78 is aligned with the hole 80. In such position the column is midway between the two extreme positions of rotation shown in FIGS. 15 and 16. The pin 78 is normally biased toward the hole 80 by a coil spring 82, and movement of the pin 80 is controlled by a cable encased in a sheath, as best seen in FIGS. 6 and 9.

Attached to the housing 44 is a fixed handle 88 of tubular construction and a second handle 90 is secured to an end of the arm 38. Within the handle 88 is a lock plunger 92 having a lock knob 94 at one end thereof. The lock plunger 93 reciprocates in spaced bushings 96, 96 and is biased toward the arm 38 by a coil spring 98, the latter being wrapped around the plunger 92. A cable anchor screw 100 is threaded into the plunger 92 and secures one end of the cable 84, as best seen in FIGS. 9 and 10. Cable clamp 105 secures the cable sheath 86 to the part of the tubular handle 88 that lies within the housing 44. The screw 100 may be optionally positioned in either a short slot 102 or in an adjacent long slot 104. These adjacent and communicating slots 102, 104 are in the tubular handle 88. When the screw 100 is in the slot 102, as shown in FIG. 9, the pin 78 will engage the hole 80 to lock the column 4 against rotation. At the same time the lock plunger 92 will engage a hole 106 in the arm 38 and lock the arm 38 to storage position, as in FIG. 3. When the knob 94 is pushed to the left (FIG. 9) and rotated about a quarter of a turn the pin 100 will then be in the longer slot 104. The force of the spring 98 will retract the plunger 92 from the hole 106 and at the same time there will be a pull on the cable 84 to release the pin 78 from the hole 80 and thereby unlock both the arm 38 and the column 4. For convenience the cable 84 and a sheath 86 may extend downwardly to the housing 44, terminating adjacent to the column 4 as shown in FIG. 6.

Figure 11:
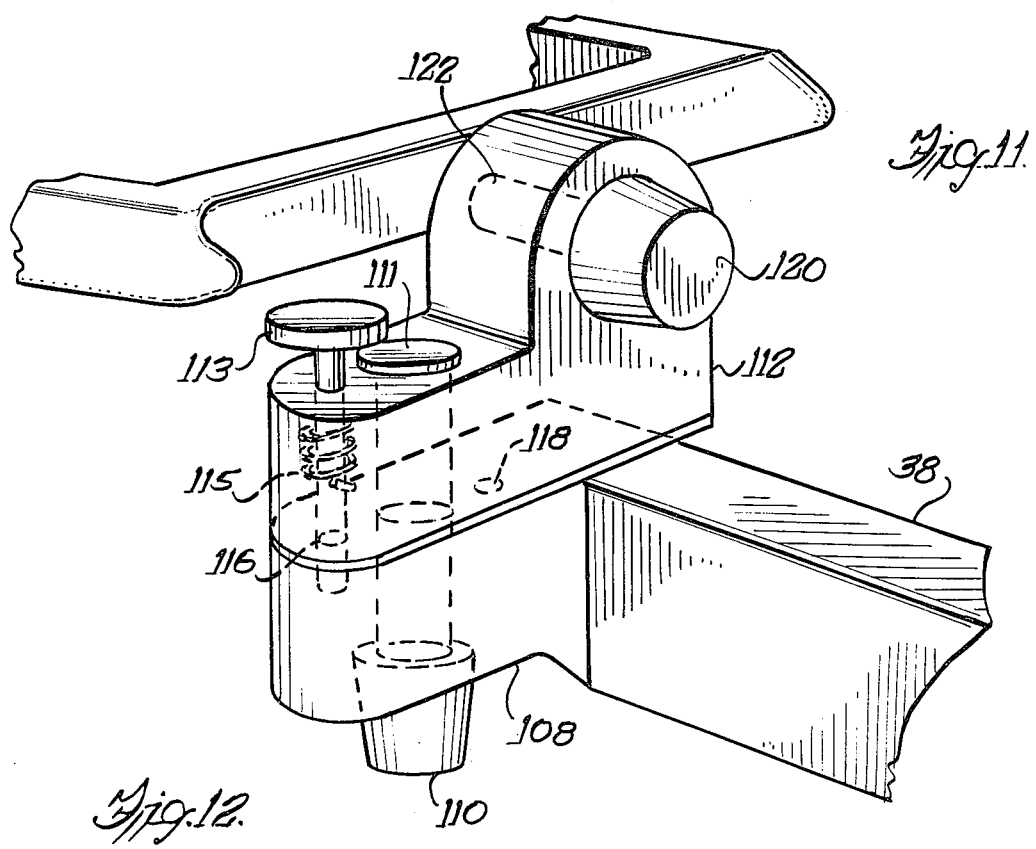
FIG. 11 is a fragmentary perspective view of the free end of the tube arm and showing the compound pivot arrangement for mounting the tube head.
Figure 12:
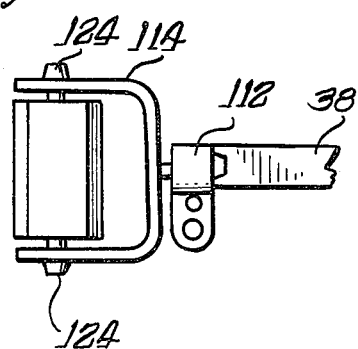
FIG. 12 is a top plan view on a reduced scale of the structure of FIG. 11 and showing the tube head and yoke in a radiographic position.
Figure 13:
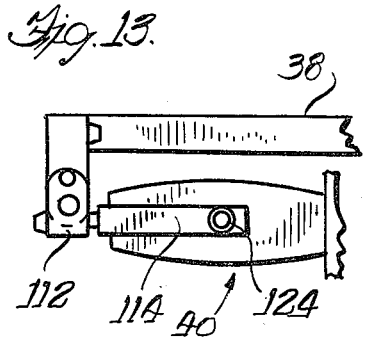
FIG. 13 is a view similar to FIG. 12 but showing the tube head in the storage and transport position.

Turning now to FIGS. 11, 12 and 13 it will be seen that the outer end of the tube arm 36 is formed with a lower pivot casting 108 having a locking nut 110 and associated pin 111 that projects therethrough and into an upper pivot casting 112. The upper pivot casting 112 rotates about the central axis of the nut 110 and pin 111 so that the upper pivot casting 112 may be rotated 180° from the position shown in FIG. 11 to that shown in FIG. 13. A spring loaded locking knob 113 is biased by spring 115 into either index hole 116 or into hole 118. Both holes 116, 118 are in the lower pivot casting and are 180° apart relative to the central axis of the locking nut 110.

A further locking nut 120 and associated pin 122 mount the tube head yoke 114 for 360° movement about the axis of the pin 122. Furthermore, the yoke 114 is formed with opposed trunions 124, 124 also permitting rotation of the tube head assembly 40 a full 360° about the trunions 124, 124. By raising the locking knob 113 the tube head can be pivoted to the position shown in FIG. 13 for transport and storage. In such position the weight of the tube head assembly tends to be substantially over the wheel 16, 16, as best seen in FIG. 3, which results in high stability in transport. Moreover, the tube head may be pivoted about the axis of the pin 113 so that it is substantially within the confines of the base 2.

The invention is claimed as follows:

1. Mobile X-ray apparatus comprising a base having a front and opposed sides, floor-engaging wheels on said base adjacent to said front and sides, a column on said base and being rotatable about a vertical axis, a carriage mounted for upward and downward movement on said column, an X-ray tube arm mounted on said carriage for movement therewith, said arm also being movable on said carriage generally horizontally relative to said base, the extent of horizontal movement of said arm and the extent of rotation of said column being such as to position an end of said arm in a number of extended locations outboard of said front and sides, an X-ray tube head assembly at said arm end; said assembly including an X-ray tube, an X-ray transformer, and a collimator; and counterweight means carried by said column and rotatable therewith for counterbalancing the tube arm and tube head assembly in said extended locations; said counterweight means including an X-ray film cassette bin plus control circuitry for operating said X-ray tube and a housing for said control circuitry.

2. Mobile X-ray apparatus according to claim 1 in which said extended locations are over an arc of substantially 180°.

3. Mobile X-ray apparatus according to claim 1 or claim 2 in which said extended locations are positions for radiographic use of the tube and in which said arm has a retracted position for locating said arm end inboard of said base, and means pivotally mounting said tube head assembly for placing the same inwardly of said arm end to a storage and transport position adjacent to said carriage.

4. Mobile X-ray apparatus comprising a base with floor-engaging wheels, a column rotatable on said base about a vertical axis 90° degrees in either direction from a predetermined reference, means for releasably locking said column at said reference against rotation, a horizontal arm projecting from said column above the base, a carriage mounting said arm on said column for horizontal and vertical movement; an X-ray tube head assembly on said arm and comprising an X-ray tube, an X-ray transformer and a collimator, and counterweighting means on said column comprising a storage bin and X-ray tube control circuitry for counterbalancing the weight of said tube head assembly as the column is rotated.

* * * * *